United States Patent [19]

Wang et al.

[11] Patent Number: 5,019,037
[45] Date of Patent: May 28, 1991

[54] PNEUMATIC RETINOPEXY INJECTOR

[75] Inventors: Carl C. T. Wang, Oakland; Leif J. Sundblom, Auburn, both of Calif.

[73] Assignee: Alcon Laboratories, Inc., Forth Worth, Tex.

[21] Appl. No.: 376,013

[22] Filed: Jul. 6, 1989

[51] Int. Cl.$^5$ .......................................... A61M 37/00
[52] U.S. Cl. ...................................... 604/23; 604/121; 604/143; 604/147; 604/294; 606/107
[58] Field of Search ................... 604/23, 26, 140, 141, 604/143, 147, 289, 290, 294, 30, 33, 34, 35, 36, 48, 51, 53, 118, 119, 121, 122; 606/107

[56] References Cited

U.S. PATENT DOCUMENTS

| | | | |
|---|---|---|---|
| 1,046,166 | 12/1912 | Flaherty | 604/121 |
| 1,105,275 | 7/1914 | Ingalls | 604/143 |
| 2,017,276 | 5/1933 | Ericson et al. | 128/218 |
| 2,484,657 | 10/1949 | Son | 604/117 |
| 2,865,371 | 12/1958 | Dorbecker et al. | 604/143 |
| 3,589,363 | 6/1971 | Banko | 128/276 |
| 3,768,472 | 10/1973 | Hodosh et al. | 128/218 |
| 3,812,855 | 5/1974 | Banko | 128/276 |
| 3,884,237 | 5/1975 | O'Malley et al. | 128/301 |
| 4,041,947 | 8/1977 | Weiss et al. | 128/276 |
| 4,177,810 | 5/1979 | Gourlandt | 128/218 |
| 4,351,335 | 9/1983 | Whitney et al. | 128/218 |
| 4,424,055 | 1/1984 | Herman | 604/36 |
| 4,508,532 | 4/1985 | Drews et al. | 604/22 |
| 4,670,006 | 6/1987 | Sinnett et al. | 604/26 |
| 4,717,384 | 1/1988 | Waldeisen | 604/143 |

FOREIGN PATENT DOCUMENTS 16647 of 1911 United Kingdom .

Primary Examiner—C. Fred Rosenbaum
Assistant Examiner—Corrine Maglione
Attorney, Agent, or Firm—Zarley, McKee, Thomte, Voorhees & Sease

[57] ABSTRACT

A pneumatic retinopexy injector includes a syringe to which is communicated a controllable gaseous pressure source. A desired volume of a gaseous substance can be injected by the syringe by utilizing a controller to introduce the pressurized gas to the syringe to cause the piston of the syringe to eject any contents of the syringe. The manual controller can comprise a foot pedal having a variable flow pneumatic valve. The invention can also utilize a vacuum source which is switchable to the syringe to allow automatic filling of the syringe.

22 Claims, 2 Drawing Sheets

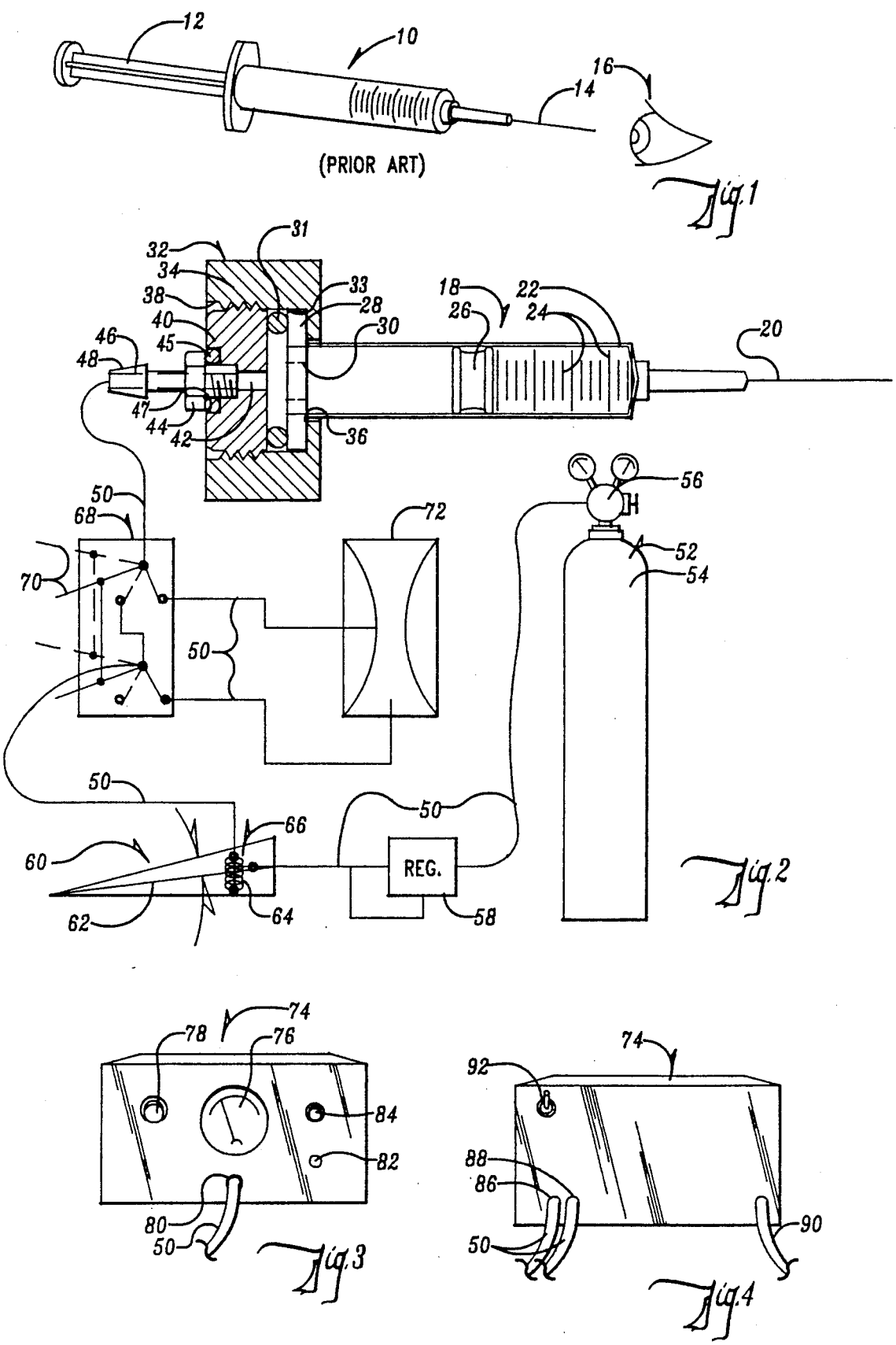

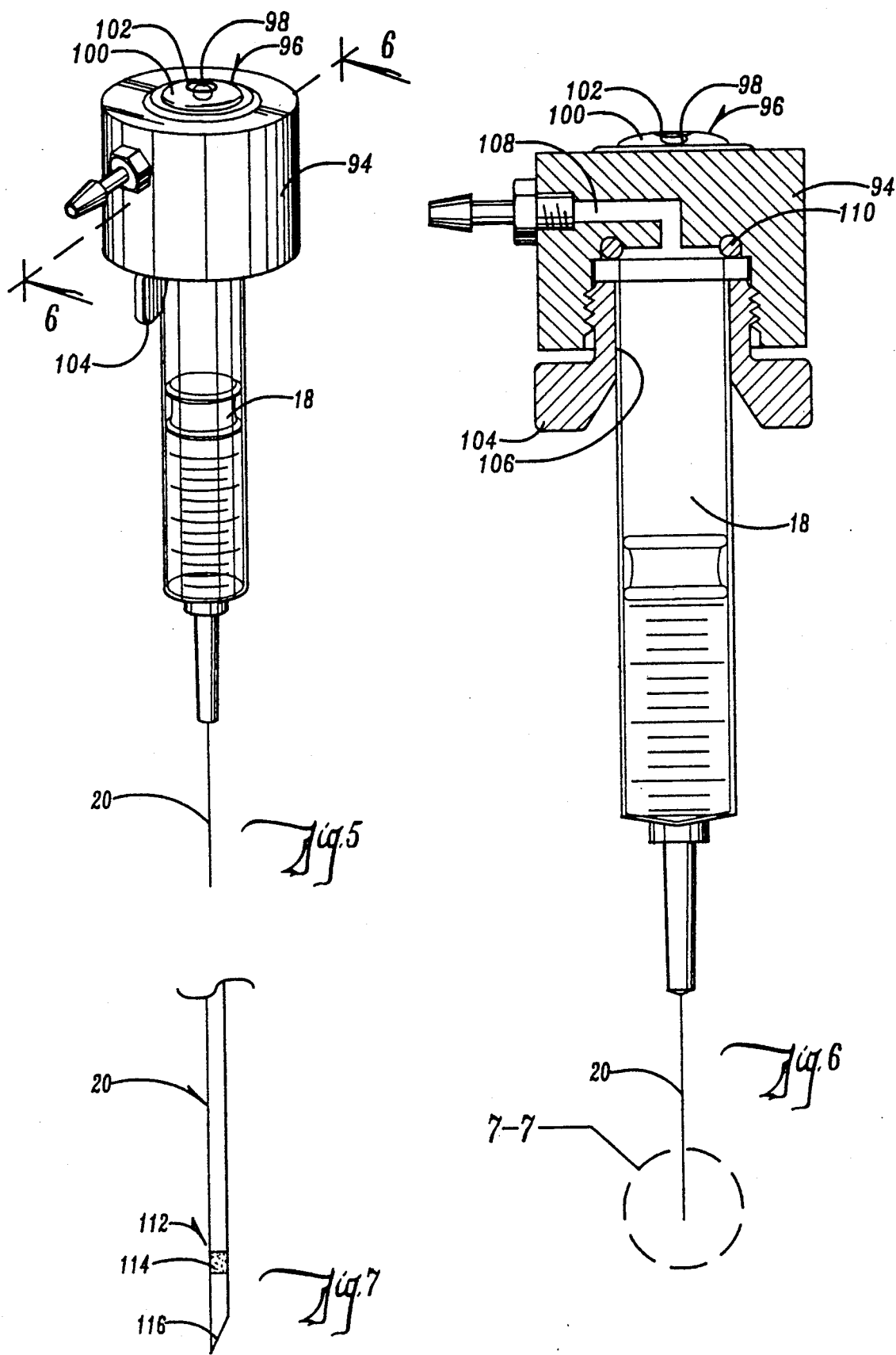

PNEUMATIC RETINOPEXY INJECTOR

BACKGROUND OF THE INVENTION a. Field of the Invention

The present invention relates to ophthalmic therapy, and in particular, methods and devices utilized in the ophthalmic theraputic procedure known as retinopexy, used in repairing partially detached and/or torn retinas.

b. Problems in the Art

Retinopexy involves injecting an air bubble to a specific location in a patient's eye to push a partially detached retina, caused by a retinal tear or break, into its appropriate position so that it can be treated for repair. It is most times used for tears or breaks in the retina located in the superior or upper portion of the eye, and which exist at or near the retina's periphery. It is advantageous in that, if successful, it eliminates the requirement of more intrusive surgery, such as intraocular surgery. This is an extremely delicate and critical procedure, as are most ophthalmic surgical procedures.

Presently, retinopexy is accomplished by utilizing a conventional handheld syringe. The ophthalmic surgeon must manually fill the conventional syringe with air or gas, manually insert the syringe needle into the patient's eye, visually monitor the location of the needle tip in the eye, and then delicately and steadily inject an accurate volume of air or gas to form a single air bubble to prop up the retina of the patient. Retinopexy injects a bubble into the eye, which migrates upwardly once expelled from the needle tip. The needle tip must be positioned very close to the damaged part of the retina and in an orientation which allows the bubble to expand and move against the tear to push it back into place.

Methods, such as are well known to those skilled in the art, are then used to cause the tear to stay in place, even after the bubble has moved or dissipated. This entire procedure thus avoids intraocular surgery and its effects and risks.

It is, of course, critically important to not only hold the needle vertically and maintain the accurate depth of the needle tip, but also to inject the gas so that one controlled-in-size bubble is formed. As can be well appreciated, this step requires a high level of skill to accomplish.

Not only does the surgeon have to accomplish all these tasks manually, usually with both hands, but also the minute parameters involved in treating the eye, along with the risk of significant damage to the eye by any unintended or unnecessary invasion of the eye, multiplies the difficulty and riskiness of such procedures.

It can therefore be seen that retinopexy with a conventional syringe requires the skill to keep the syringe as vertical as possible, insert the needle tip so as not to damage any other structure of the eye, such as the lens, position the needle tip appropriately to the required depth and location, and then operate the syringe satisfactorily to produce the necessary type of bubble, and the necessary location. Moreover, the surgeon must most times utilize some sort of a light source and magnification lens or scope to provide an adequate view of the needle tip in the eye.

The problems involved in present retinopexy methods reveal the need for improvements in this procedure. Operating a conventional syringe under such conditions requires reliance on a steady, correctly positioned, finely controlled injection by the surgeon's hands. Conventional needles are prone to injecting bubble trains, instead of one bubble. This could be the result of faulty expulsion of the gas from the syringe. Small bubbles and bubble trains usually cannot support the retina in the manner needed or they may obscure the surgeon's vision of the retinal damage. Furthermore, they may even pass through the retinal break, if small enough, and therefore provide opposing pressure to defeat the retinopexy procedure.

If the surgeon concentrates too much on steady injection of the gas to form a correct bubble, small movements in the needle tip may result in misplacement of the bubble.

The critical nature of the retinopexy procedure currently depends entirely on manual control of the conventional syringe. This simply is just not as reliable as might be desired in the art.

It is therefore a principal object of the present invention to improve over or solve the deficiencies and problems in the art.

Another object of the present invention is to provide a pneumatic retinopexy injector which eliminates a significant amount of reliance on manual control by the surgeon.

A further object of the present invention is to provide an injector as above described which is highly controllable.

Another object of the present invention is to provide an injector as above described which provides improved results for retinopexy.

A further object of the present invention is to provide an injector as above described which produces a reliable gas bubble for retinopexy.

Another object of the present invention is to provide an injector as above described which provides a controlled volume injection rate for retinopexy procedures.

Another object of the present invention is to provide an injector as above described which provides a controlled displacement rate for retinopexy procedures.

A further object of the present invention is to provide an injector as above described which is economical, efficient, reliable, and durable.

Another object of the present invention is to provide an injector as above described which is easily usable for repeated retinopexy procedures.

Another object of the present invention is to provide an injector as above described which facilitates easy filling.

These and other objects features and advantages of the present invention will become more apparent with reference to the accompanying specification and claims.

SUMMARY OF THE INVENTION

The present invention is a pneumatic retinopexy injector for improved control of air or gas during retinopexy procedure. A syringe means is connected in fluid communication to a pressure source. The pressure source provides the power to move the plunger or piston of the syringe according to operation of a control means by the surgeon.

The surgeon therefore can concentrate on accurate placement of the needle of the syringe with his/her hand or hands, and then can operate injection of the gaseous contents of the syringe by operation of the control means.

The control means can comprise a foot pedal or other manually actuated control which is removed from the syringe. By appropriate control, the force from the pressure source can be marshalled to provide the needed steady and controlled ejection of gas through the syringe. The invention provides volume injection rate or displacement rate which is highly accurate and controllable.

Optional features are allowed with the present invention. Means can be included for semi-automatic filling of gas or air into the syringe. Regulation means can be utilized to more accurately control the force provided by the pressure source.

The control module can also contain gauges and indicators to assist the surgeon in monitoring operation of the procedure, and to adjust the parameters of operation of the device.

A perpendicularity gauge and a depth indicator can also be incorporated with the injector to allow a user to easily monitor and ensure that correct positioning of the injector with respect to gravitional pull, and that desired injection depth is maintained during the procedure.

BRIEF DESCRIPTION OF THE DRAWINGS

FIG. 1 is a perspective and schematic depiction of the prior art for retinopexy.

FIG. 2 is a schematic depiction of a preferred embodiment of the present invention.

FIG. 3 is a front elevational view of a control module for the present invention.

FIG. 4 is a rear elevational view of the control module of FIG. 3.

FIG. 5 is a perspective view of an alternative embodiment of a hand piece according to the invention including a perpendicularity gauge.

FIG. 6 is a sectional view taken along line 6—6 of FIG. 5.

FIG. 7 is an isolated view of the portion outlined by line 7—7 of FIG. 6 showing a depth gauge or indicator for the invention.

DETAILED DESCRIPTION OF THE PREFERRED EMBODIMENT

In order to aid in an understanding of the invention, a preferred embodiment of the invention will now be described. Reference should be taken to the drawings. Reference numerals will be utilized to identify various parts and components as depicted in the drawings.

In particular reference to FIG. 1, there is depicted the prior art method of retinopexy. A conventional syringe 10 is utilized by the opthalmic surgeon to perform the procedure. Gas or air is drawn into syringe 10, as is conventionally known, by pulling back plunger or piston handle 12. Needle 14 is then introduced into the patient's eye 16. The surgeon monitors the location of the end of needle 14 and then attempts to steadily push the plunger handle 12 inwardly to eject a desired volume of gas to form a bubble for retinopexy.

The problems with this procedure have been previously described.

FIG. 2 depicts a preferred embodiment of the present invention which has been entitled "Pneumatic Retinopexy Injector". An automated syringe handpiece 18 replaces the conventional syringe 10 of the prior art embodiment in FIG. 1. Handpiece 18 consists of a fine gauge needle 20 (preferred to be 30 gauge or 30g), a syringe body 22 with volume markings 24, and a plunger head or piston 26 movable within body 22. As is well understood in the art, plunger head 26 is made of a material which can seal against the inside of syringe body 22, yet with sufficient force applied to it can slidably move in body 22.

In this preferred embodiment of FIG. 2, syringe body 22 has a rear flange 28 which surrounds an aperture 30 through which fluid communication is accomplished. Syringe body 22 is mounted in a base 32 which includes a member 34 which includes an aperture 36 and a threaded aperture 38 in opposite ends. Syringe body 22 can be inserted through threaded aperture 38 and aperture 36. Rear flange 28, being larger in diameter than aperture 36, seats syringe body 22 in the position shown in FIG. 2. Threaded cap 40 is then threaded down into threaded aperture 38 to securely mount the syringe body 22 in that position. This arrangement allows for easy replacement of syringe body 22 and needle 20 for each procedure. An elastomeric O-ring 31 can be seated in groove 33 in base 32 so as to create a seal between base 32 and threaded cap 40.

The threaded cap 40 includes a central bore 42 through its middle which communicates with the aperture into syringe body 22. Central bore 42 thus provides the fluid access into syringe body 22.

A threaded connection 44 is threadably mountable onto threaded cap 40 and also has a bore 46 therethrough. In the preferred embodiment, threaded connection 44 can include a tapered connector 48, such as is well known in the art, for air tight connection of flexible tubing. An O-ring 45, in ring seat 47, is configured of an elastomeric material to prevent fluid leakage between threaded cap 40 and threaded connection 44.

In the remainder of FIG. 2, tubing 50 is schematically represented as shown. A pneumatic pressure source 52, in the preferred embodiment, comprises a gas pressure supply tank 54, such as is well known in the art. Supply tank 54 has a step down regulator (preferably less than 60 pounds per square inch (psi)) 56, with appropriate gauges and on/off valve. In the preferred embodiment, supply tank 54 can hold pressurized air, pressurized gas, or a mixture of the two.

Supply tank 54 is put into fluid communication with pressure regulator 58 by tubing 50. Regulator 58 is used in the preferred embodiment to further allow control of pressurized gas from supply tank 54, but is not necessarily needed for operation of the invention. Regulator 58 can be used to regulate the pressure of the regulated gas from supply tank 54, as is well understood by those skilled in the art, according to the desire of the surgeon.

The control member 60 of the present invention in FIG. 2 comprises a foot pedal 62. Pedal 62 is biased to a normally closed position by a spring 64. In the preferred embodiment, foot pedal 62 includes a variable flow pneumatic control 66 which is connected by tubing 50 to regulator 58. Variable flow control 66 operates as follows. With no foot pressure applied to pedal 62, spring 64 holds it in a up or raised position which closes any fluid pathway through pedal 62. Upon compression of pedal 62, variable flow control 66 operates to allow pressurized gas to pass through pedal 62 at a rate proportional to depression of pedal 62. The surgeon can therefore have accurate and reliable control of pressure from supply tank 54.

Tubing 50 then puts pedal 62 in fluid communication with switch device 68. As can be seen in FIG. 2, switch control 70 is schematically depicted and allows selection between a "fill" mode and an "inject" mode.

Tubing 50 connects handpiece 18 to switch device 68, along with a pressure to vacuum convertor 72. Switch device 68 is analogous to a double pole, a single throw electrical switch. In the position shown in solid lines in FIG. 2, switch control 70 is in the "fill" mode position. Fluid pathways are created between foot pedal 62, pressure to vacuum convertor 72, and handpiece 18. Upon depression of foot pedal 62, regulated and controlled pressurized gas flows into pressure to vacuum convertor 72, causing creation of sub-atmospheric pressure at threaded connection 44 of handpiece 18. This would in turn cause plunger head 26 to be pushed by the atmospheric pressure on the needle side of syringe body 22 towards rear flange 28 of syringe body 22. Filling of the controlled volume of air gas could then be accomplished. When a sufficient volume is filled into syringe body 22, foot pedal 62 would be released and filling would stop.

Conversely, if switch control 70 was moved to the position shown by dash lines in FIG. 2, the fluid pathway through pressure to vacuum convertor 72 would be closed off. A direct fluid pathway between foot pedal 62 and handpiece 18 would then be created.

If syringe body 22 is filled with the desired quantity of gas or air, foot pedal 62 would then be operated by the surgeon depressing it to cause the super-atmospheric pressure to be imposed on the rear flange side of the plunger head 26 to force it to move towards the needle side of syringe body 22, to eject the gas or air from syringe body 22 into the eye.

It is to be understood that by utilizing regulator 58 and foot pedal 62, reliable and flexible control of the amount and speed of injection can be accurately controlled by the surgeon. The surgeon's concentration can be an accurate placement of needle 20 of handpiece 18. Ejection/injection of the gas can then be accomplished, without impacting on positioning the needle 20, by operation of the foot pedal. The surgeon can determine the amount of gas to be injected by the amount which is filled into syringe body 22, or by operation of the foot pedal 62.

FIGS. 3 and 4 simply depict control module 74, which could be an embodiment to house switch device 68, pressure to vacuum convertor 72, and regulator 58. As shown in FIG. 3, an appropriate pressure gauge 76 can show the surgeon information regarding pneumatic pressure. Other gauges or indicators could also be used. A rotary dial 78 could be utilized to control pressure regulator 58 to set the level of pneumatic pressure available to foot pedal 62. A port 80 can be utilized to attach tubing to handpiece 18. An indicator light 82 could be utilized to show the electrical powers being supplied to the unit, or for some other indication purposes. Other controls such as knob 84 could be utilized.

In FIG. 4, for illustration purposes, it is shown that ports 86 and 88 could be used with tubing to connect to foot pedal 62. Cable 90 could be utilized for connection to an electrical power source. A switch 92 could be utilized for switch control 70 of switch device 68.

FIGS. 5-7 depict alternative enhancements for the pneumatic retinopexy injector set forth above. These enhancements are optional only and are intended to facilitate advantageous use of the invention.

FIGS. 5 and 6 depict an automated syringe handpiece essentially identical to handpiece 18 previously described. The only differences are that threaded connection 44 and tapered connection 48 of handpiece 18 in FIG. 2 are moved to the side of the base, in FIG. 5 designated by reference numeral 94. On top of base 94 is a perpendicularity gauge 96, which in the embodiment of FIG. 5 comprises an air-bubble level. Air bubble 98 is housed within fluid filled transparent convex cover 100. As depicted in FIGS. 5 and 6, when the handpiece and needle are directly perpendicular to the earth's surface (that is, directly aligned with the earth's gravitational pull), bubble 98 seeks out and finds center target 102, indicating that the entire handpiece is "perpendicular". In this position fluid transfer is believed to best be performed.

By being able to quickly tell if the handpiece is perpendicular, enhances the ability for effective and safe pneumatic retinopexy. Any movement out of perpendicular can thus be easily detected.

FIG. 6 shows in detail how base 94 can be connected to rear flange 28 of syringe body 22. A threaded cap 104 having an interior aperture 106 can threadably mate with base 94 through syringe body 22 to secure base 94 to rear flange 28. A bore 108 through base 94 can assume an L-shaped path out to threaded connection 44 and tapered connector 48. An O-ring 110 can assist in sealing between base 94 and rear flange 28 of syringe body 22. This allows the top of base 94 to have positioned on it the perpendicularity gauge 96 for easy viewing and effective operation.

The handpiece of FIGS. 5 and 6 would operate in all other respects the same as the embodiment of FIG. 2 for the retinopexy procedure.

FIG. 7 shows in detail another optional enhancement for the invention. To assist in the effectiveness and safety of the pneumatic retinopexy procedure, it can also be advantageous to include a depth indicator 112 on to needle 20. Depth indicator 112 in the preferred embodiment, can consist of a marked band at a predetermined location away from the level 116 of needle 20. During retinopexy procedure, the user of the instrument can therefore easily and effectively observe when the needle 20 has been inserted in the desired, predetermined depth into the eye. This enhances effectiveness and safety of retinopexy procedure as it has been found important to perform the procedure at a certain depth. Many times in retinopexy, the needle tip is inserted into the eye a small distance past the depth at which the bubble will be ejected. This is to ensure that the needle has penetrated sufficiently. The depth indicator 112 can therefore allow the surgeon to easily have a reference point and can reliably withdraw the needle to the depth indicated by depth indicator 112.

In preferred embodiment, mark band 114 can be applied to needle 20 by an easily visually detectable coating such as paint or a band of material secured to needle 20, or can be etched or otherwise manufactured into the needle. Other means and manners of making of a visually discernible marking are also possible.

It is believed desirable that in pneumatic retinopexy, the needle depth be somewhere between 0.5 to 4 mm inside the eye cavity. In the preferred embodiment of FIG. 7, mark band 114 is 1 mm wide centered at 3 mm from level 116. The user of the instrument would therefore know when the needle has been inserted approximately 3 mm, and would know when the depth approaches 4 mm if the mark band 114 disappears into the wound in the eye.

It is to be understood that different types of markings, at different positions on needle 20 can be utilized if desired.

Operation of the preferred embodiment of the invention has been set forth in the above description. It is to be understood that the included preferred embodiment is given by way of example only, and not by way of limitation to the invention, which is solely described by the claims herein. Variations obvious to one skilled in the art will be included within the invention defined by the claims.

For example, in the preferred embodiment of FIG. 2, pressure to vacuum convertor 72 is a Venturi vacuum generator, such as is well known in the art. Tapered connector 48 could be a locking luer connection, such as are well known.

As is obvious, filling of the syringe body with the gas or air to be injected, must be accomplished by first moving the plunger head or piston 26 completely forward to the needle end syringe body 22. Reverse movement of plunger head 26 would then draw the gas or air into syringe body 22. Alternatively, syringe body 22 could be filled by communicating a gas or air within a high pressure container with needle 20. The pressurization would then automatically load the air gas into syringe body 22.

It can also be seen that if syringe body 22 is filled to more than the desired injection volume, operation of the system can be completed so that any excess is ejected before needle 20 is inserted into the eye. It is to be understood that in the preferred embodiment, injection pressure is generally desired to be between 0 and 30 psig. It is preferred that supply tank 54 contain on the order of 2,000 psi, and that step down regulator 56 have a setting of at or less than 60 psi. This arrangement will provide for as many operations as possible without the need of recharging supply tank 54.

Injection pressure can be as low as 2 psig. On the other hand, for filling syringe body 22, pressure to vacuum convertor 72, if a Venturi nozzle, needs to generate approximately −2 psig.

It is to be understood that injection pressure, pressure in supply tank 54, and stepped-down regulation of pressure can differ from the value set forth above and still stay within the boundaries of the invention. Furthermore, the level of injection pressure and/or level of negative pressure generated by pressure to vacuum convertor 72 can vary and stay within the boundaries of the invention. These levels are set forth with regard to this description of the preferred embodiment of the invention only.

It is also to be understood that the present invention is adaptable and flexible to various situations. It is to be understood that the gas injection rate is dependent on loading factors such as plastic-rubber or glass-rubber friction, syringe diameter, needle gauge and length, nature of the tissue at the terminal end of the injection needle, and a host of other variables. The present invention allows a controlled volume injection rate, or, for a given syringe piston, a controlled displacement rate.

Also, it is to be understood that control member 60, while preferred to be a foot pedal, could be some other type of controller. For example, it could be a hand-controlled device or some other manually actuated device. It is preferred, as with variable flow control 66 in foot pedal 62, that control member 60 have a flow sensitive valve which will increase flow proportional to control actuation.

In the preferred embodiment, pressure to vacuum convertor 72 is to be driven by approximately 30 psi. Filling of syringe body 22 can also be accomplished by removing needle 20, attaching a pressurized source of gas to syringe body 22, which will cause the plunger head 26 to move away until the desired volume has been reached.

Other examples of options are to replace any pneumatic valves with electomechanical valves. The pressure regulators can be replaced with an electronic pressure controller. The pneumatic switch can also be replaced with a momentary electric switch for gas filling.

It can therefore be seen that the invention achieves at least all of its stated objectives. It enhances the reliability and effectiveness of retinopexy., especially for the superior part of the eye, and avoids intraocular surgery. The invention is particularly useful if the retina is partially detached caused by a retinal tear or break in the eye. The invention provides for a safe and effective pneumatic retinopexy allowing controlled volume injection or controlled displacement rate to the eye. Optional enhancements also contribute to the effectiveness and safety of the invention. The use of the perpendicularity gauge and/or depth indicator provide easily useable and reliable objective references, making the procedure much safer.

What is claimed is:

1. A retinopexy injector means comprising:
   syringe hand tool means for manipulation and placement by the hands of a surgeon to inject a gaseous substance into a specific location in a patient's eye to produce a gas bubble to assist in holding a partially detached or damaged retina in position for treatment, the syringe hand tool means including an injection needle connected in fluid communication directly to one end of a syringe case having an interior wall within which a piston means is movable between a first position and a second position nearer the injection needle, the piston means including a piston head in sealing contact with the interior wall of the syringe case, but being movable within the syringe case between the first and second positions according to a controllable pressure on the piston means;
   communication means for operative attachment of and in fluid communication between the syringe hand tool means operatively attaching and a gaseous pressure means for providing the controllable pressure to move the piston means from the first position to the second position; and
   a control means connected in fluid communication between the syringe hand tool means and the gaseous pressure means for allowing selective control of delivery of the controllable pressure to the piston means.

2. The injector of claim 1 wherein the syringe hand tool means is removably mounted in a base means, the base means having connection means for attachment to fluid communication tubing for communication with the gaseous pressure means.

3. The injector of claim 1 wherein the gaseous pressure means comprises a pressurized gas supply tank which includes a regulation means in fluid communication with the gaseous pressure means.

4. The injector means of claim 1 wherein the control means comprises a variable flow pneumatic valve.

5. The injector means of claim 4 wherein the valve is controllable by a manually operated control associated with the valve.

6. The injector means of claim 5 wherein the manual control comprises a spring biased foot pedal means.

7. The injector means of claim 1 further comprising an adjustable variable pressure regulation means connected in fluid communication between the gaseous pressure means and the control means.

8. The injector means of claim 1 further comprising a vacuum generation means and a switch for putting a vacuum in fluid communication with the syringe case.

9. The injector means of claim 8 wherein the vacuum generation means includes a pressure to vacuum convertor means.

10. The injector means of claim 9 further comprising a pneumatic switch means positioned in fluid communication between the control means and the syringe means, and between the pressure to vacuum convertor means and the syringe means, to allow selection between pressure and vacuum to the syringe means.

11. The injector means of claim 1 further comprising a perpendicularity gauge means operatively associated with the injector means to provide an indication of the perpendicularity of the injector means.

12. The injector means of claim 11 wherein the perpendicularity gauge means indicates perpendicularity with regard to the earth's surface.

13. The injector means of claim 11 wherein the perpendicularity gauge means comprises a level means including an air bubble within a sealed fluid chamber.

14. The injector means of claim 13 wherein the indicia comprises a visually distinct band at a predetermined distance from the tip of the needle along the needle.

15. The injector means of claim 1 further comprising a depth indicator means including perceivable indicia means positionable along the injection needle for showing distance from the tip of the injection needle to the indicia, the indicia allowing perception of depth of insertion of the needle during retinopexy procedure.

16. A pneumatic retinopexy injector means comprising:
    syringe means for injecting a gaseous substance into a patient's eye to produce a gas bubble to assist in holding a partially detached or damaged retina in position for treatment;
    the syringe means including an injection needle connected in fluid communication with a syringe body within which a piston is movable between at least a partially filled position and a discharge position;
    the syringe body including a flange means at its end opposite from the end connected to the needle;
    a base member comprising a first portion having a variable width bore therethrough;
    the syringe body passing through a narrowed portion of the bore, but the flange of the syringe body seating against shoulders surrounding the narrowed portion of the bore, to allow seating of the syringe body in the base member;
    cap means, releaseably securable to the first portion of the base means, for securing the syringe body into the base portion; and
    aperture means in the base means for providing fluid communication through the base member to the interior of the syringe body.

17. A method for pneumatic retinopexy injection comprising:
    providing a fluid pathway to the interior of a syringe having a movable piston therein and a needle associated therewith;
    filling a desired volume of a gaseous substance into the syringe on one side of the piston; and
    controlling the introduction of a regulated pressurized gas to the syringe on the other side of the piston to expel the gaseous substance into a patient's eye for a retinopexy procedure.

18. The method of claim 18 wherein control of pressurized gas is accomplished by a manual control comprising a manually operated variable flow pneumatic valve.

19. The method of claim 18 wherein the manual control is a foot pedal.

20. The method of claim 17 further comprising generating a subatmospheric pressure by a sub-atmospheric pressure means and connecting, in fluid communication, the syringe means on the one side of the piston with the sub-atmospheric pressure to facilitate filling of the syringe with a gas or air.

21. The method of claim 17 further comprising controlling position of the syringe with respect to a patient's eye during the retinopexy procedure by monitoring perpendicularity of the syringe with the earth, the monitoring being accomplished by referencing an air-bubble level associated with the syringe.

22. The method of claim 17 further comprising monitoring depth of insertion of the needle of the syringe into a patient's eye by monitoring a marking on the needle positioned a predetermined depth from the tip of the needle.

* * * * *